US011819521B2

(12) United States Patent
Deitcher

(10) Patent No.: US 11,819,521 B2
(45) Date of Patent: *Nov. 21, 2023

(54) CELLULAR COMPOSITIONS DERIVED FROM PRIOR ORGAN DONORS AND METHODS OF MANUFACTURE AND USE THEREOF

(71) Applicant: MEDEOR THERAPEUTICS, INC., South San Francisco, CA (US)

(72) Inventor: Steven R. Deitcher, San Mateo, CA (US)

(73) Assignee: MEDEOR THERAPEUTICS, INC., South San Francisco, CA (US)

( * ) Notice: Subject to any disclaimer, the term of this patent is extended or adjusted under 35 U.S.C. 154(b) by 476 days.

This patent is subject to a terminal disclaimer.

(21) Appl. No.: 17/072,128

(22) Filed: Oct. 16, 2020

(65) Prior Publication Data

US 2021/0030809 A1  Feb. 4, 2021

Related U.S. Application Data

(63) Continuation of application No. 15/946,124, filed on Apr. 5, 2018, now Pat. No. 10,842,821.

(51) Int. Cl.
  *A61K 35/28* (2015.01)
  *A61K 35/12* (2015.01)

(52) U.S. Cl.
  CPC ........ *A61K 35/28* (2013.01); *A61K 2035/122* (2013.01); *A61K 2035/124* (2013.01)

(58) Field of Classification Search
  None
  See application file for complete search history.

(56) References Cited

U.S. PATENT DOCUMENTS

| | | | |
|---|---|---|---|
| 5,607,579 A | 3/1997 | Latham, Jr. et al. | |
| 5,772,994 A | 6/1998 | Ildstad et al. | |
| 5,876,708 A | 3/1999 | Sachs | |
| 6,280,957 B1 | 8/2001 | Sayegh et al. | |
| 6,544,506 B2 | 4/2003 | Reisner | |
| 6,558,662 B2 | 5/2003 | Sykes et al. | |
| 6,743,192 B1 | 6/2004 | Sakota et al. | |
| 6,877,514 B2 | 4/2005 | Sykes | |
| 7,270,810 B2 | 9/2007 | Reisner et al. | |
| 7,288,255 B1 | 10/2007 | Shlomchik et al. | |
| 7,297,329 B2 | 11/2007 | Akashi et al. | |
| 7,332,157 B2 | 2/2008 | Sykes | |
| 7,638,121 B2 | 12/2009 | Sykes | |
| 7,776,591 B2 | 8/2010 | Xia et al. | |
| 7,811,815 B2 | 10/2010 | Brown | |
| 7,939,062 B2 | 5/2011 | Sykes | |
| 8,632,768 B2 | 1/2014 | Ildstad et al. | |
| 8,734,786 B2 | 5/2014 | Miller et al. | |
| 8,916,147 B2 | 12/2014 | Reisner | |
| 8,980,329 B2 | 3/2015 | Brown | |
| 9,090,871 B2 | 7/2015 | Durrant et al. | |
| 9,364,600 B2 | 6/2016 | Pages et al. | |
| 9,452,184 B2 | 9/2016 | Ildstad et al. | |
| 9,504,717 B2 | 11/2016 | Strober et al. | |
| 9,545,427 B2 | 1/2017 | Brown | |
| 9,561,253 B2 | 2/2017 | Strober et al. | |
| 9,678,062 B2 | 6/2017 | Ildstad et al. | |
| 9,695,394 B1 | 7/2017 | Coelho et al. | |
| 10,603,340 B2 | 3/2020 | Strober et al. | |
| 11,435,350 B2 | 9/2022 | Zdanowski et al. | |
| 2002/0107469 A1 | 8/2002 | Bolan et al. | |
| 2008/0199949 A1 | 8/2008 | Alroy | |
| 2010/0042015 A1 | 2/2010 | Brown | |
| 2010/0310588 A1 | 12/2010 | Bluestone et al. | |
| 2011/0110909 A1 | 5/2011 | Ildstad et al. | |
| 2012/0177621 A1 | 7/2012 | Strober et al. | |
| 2012/0329668 A1 | 12/2012 | Sarwal et al. | |
| 2014/0004085 A1 | 1/2014 | Kaplan | |
| 2014/0369974 A1 | 12/2014 | Reisner et al. | |
| 2016/0046974 A1 | 2/2016 | Efcavitch et al. | |
| 2017/0106086 A1 | 4/2017 | Strober et al. | |
| 2018/0221410 A1 | 8/2018 | Strober et al. | |
| 2019/0225940 A1 | 7/2019 | Vo Linda et al. | |
| 2019/0358269 A1 | 11/2019 | Reisner et al. | |
| 2021/0189344 A1 | 6/2021 | Veale et al. | |

FOREIGN PATENT DOCUMENTS

| | | | |
|---|---|---|---|
| EP | 2606120 B1 | 10/2015 | |
| WO | 1995003062 A1 | 2/1995 | |
| WO | 2002040640 A2 | 5/2002 | |
| WO | 2003012060 A2 | 2/2003 | |
| WO | 03101201 A1 | 12/2003 | |
| WO | 2011068829 A1 | 6/2011 | |
| WO | 2012024427 A2 | 2/2012 | |
| WO | 2012096974 A1 | 7/2012 | |
| WO | 2013093919 A2 | 6/2013 | |
| WO | 2014133729 A1 | 9/2014 | |
| WO | 2015/172080 A1 | 11/2015 | |
| WO | 2016/201111 A1 | 12/2016 | |
| WO | 2017/005647 A1 | 1/2017 | |

OTHER PUBLICATIONS

Acenocoumarol from Wikipedia, the free encyclopedia pp. 1-3, downloaded Sep. 26, 2022.
Ades, 1989, Cell suspension from collagenase digestion of bone matton trephine biopsy specimens, Journal of Clinical Pathology, 42:427-432.
Aldenhoven, 2017, Quality of life of Hurler syndrome patients after successful hematopoietic stem cell transplantation, Blood Adv, 1(24):2236-2242.
Arber, 2016, The 2016 revision to the World Health Organization classification of myeloid neoplasms and acute leukemia, Blood, 127(20):2391-2405.
Bagul, 2008, Experimental renal preservation by normothermic resuscitation perfusion with autologous blood, British Journal of Surgery, 95:111-118.

(Continued)

*Primary Examiner* — Michelle F. Paguio Frising
(74) *Attorney, Agent, or Firm* — Brown Rudnick LLP; Adam M. Schoen

(57) ABSTRACT

The invention provides methods of making and using compositions for establishing mixed chimerism in a subject that include $CD34^+$ cells and $CD3^+$ cells derived from an apheresis product obtained from a subject that has previously donated a solid organ.

19 Claims, No Drawings

(56) References Cited

OTHER PUBLICATIONS

Bone marrow examination from Wikipedia, the free encyclopedia, pp. 1-5, downloaded Sep. 27, 2022.
Camitta, 1975, Selection of patients for bone marrow transplantation in severe aplastic anemia, Blood 45(3):355-363.
Czerw, 2016, High CD3+ and CD34+ peripheral blood stem cell grafts content is associated with increased risk of graft-versus-host disease without beneficial effect on disease control after reduced-intensity conditioning allogeneic transplantation from matched unrelated donors for acute myeloid leukemia, Oncotarget, 7(19):27255-27266.
Extended European Search Report issued in European Application No. 19781109.4, dated Feb. 17, 2022, 6 pages.
Extended European Search Report issued in European Application No. 19782310.7, dated Feb. 17, 2022, 7 pages.
Extended European Search Report issued in European Application No. 19861568.4, dated Jun. 1, 2022, 7 pages.
Extended European Search Report issued in European Application No. 20748810.7, dated Oct. 20, 2022, 10 pages.
Greenberg, 2016, Cytopenia levels for aiding establishment of the diagnosis of myelodysplastic syndromes, Blood, 128(16):2096-2097.
Heparin from Wikipedia, the free encyclopedia, pp. 1-12, downloaded on Sep. 26, 2022.
Hildebrandt, 2000, Immunomagnetic selection of CD34+ cells: factors influencing component purity and yield, Transfusion, 40:507-512.
Kaloutsi, 1994, Comparison of Bone Marrow and Hematologic Findings in Patients with Human Immunodeficiency Virus Infection and Those with Myelody splastic Syndromes and Infectious Diseases, American Journal of Clinical Pathology, 101(2):123-129.
Koeppen, 2016, DOrsal root ganglia in Friedreich ataxi: satellite cell proliferation and inflammation, Acta Neuropathologica Communications 4:46.
Konieczna, 2013, Human Immunology, Abstracts, 74:35-OR.
Levesque, 2008, Mobilization of hematopietic stem cells: state of the art, Current Opinion in Organ Transplantation 13:53-58.
Link, 1995, Combined transplantation of allogeneic bone marrow and CD34+ blood cells, Blood 86(7):2500-2508.
Machalinski, 2003, An optimization of isolation of early hematopoietic cells from heparinized cadaveric organ donors, Transplantation Proceedings 35:3096-3100.
Marsh, 2009, Guidelines for the diagnosis and management of aplastic anaemia, Br J Haematol 147(1):43-70.
Mathew, 1998, Cellular immune responses of human cadaver donor bone marrow cells and their susceptibility to commonly used immunosuppressive drugs in transplantation, Transplantation, 66(7):947-955.
Merriam-Webster, definition for "exsanguination", retrieved from internet Sep. 23, 2022.
Monroy, 1987, The effect of recombinant GM-CSF in the recovery of monkeys transplanted with autologous bone marrow, Blood 70(5):1696-1699.
Montane, 2008, Epidemiology of aplastic anemia: a prospectice multicenter study, Haematologica, 93(4):518-523.
Reddy, 2021, Therapeutic Apheresis in Transfusion Medicine, J McCullough (Ed.) https://doi.org/10.1002/9781119599586.ch20 Chapter 20, pp. 500-540.
Shapiro, 2017, Bone Marrow aspiration for regenerative orthopedic intervention: technique with ultrasound guidance for needle placement, Regenerative Medicine, 12:8, 917-928.
Trepanning, from Wikipedia, the free encyclopedia pp. 1-7, downloaded Sep. 27, 2022.
Yousefi, 2018, Producing Covalent Microarrays of Amine-Conjugated DNA Probes on Various Functional Surfaces to Create Stable and Reliable Biosensors, Advanced Materials Interfaces, 5(16):1800659.

Yu, 2016, G-CSF and hypoxic conditioning improve the proliferation, neural differentiation and migration of canine bone marrow mesenchymal stem cells, Experimental and Therapeutic Medicine, 12:1822-1828.
Zuber, 2017, Mechanisms of Mixed Chimerism-Based Transplant Tolerance, Trends in Immunology, 38(11):829-843.
Alexander, 2008, Chimerism and Tolerance in a Recipient of a Deceased-Donor Liver Transplant, N Engl J Med, 358:369-74.
Arai, 2015, Increasing Incidence of Chronic Graft-versus-Host Disease in Allogeneic Transplantation: A Report from the Center for International Blood and Marrow Transplant Research, Biol Blood Marrow Transplant, 21:266-274.
Arbab, 2004, Efficient Magnetic Cell Labeling with Protamine Sulfate Complexed to Ferumoxides for Cellular MRI Blood, American Soc. of Hematology, 104(4):1217-1223.
Bakhuraysah, 2016, Hematopoietic stem cell transplantation for multiple sclerosis: is it a clinical reality? Sem Cell Res Ther. 2016; 7:12, 12 pages.
Beelen, 2000, Transplantation of highly purified HLA-identical sibling donor peripheral blood CD34+ cells without prophylactic post-transplant immunosuppression in adult patients with first chronic phase chronic myeloid leukemia: results of a phase II study, Bone Marrow Transplantation, 823-829, 26, Macmillan Publishers Ltd., Basingstoke, United Kingdom.
Dick, 1997, Assay of human stem cells by repopulation of NOD/SCID mice, Stem Cells, 1997;15 Suppl 1:199-203.
Field, 2001, Tolerance, mixed chimerism and protection against graft-versus-host disease after total lymphoid irradiation, Phil. Trans. R. Soc. Lond. B, 356:739-748.
Frisch, 2014, Hematopoietic Stem Cell Cultures and Assays, Methods Mol Biol. 2014; 1130: 315-324.
Fudaba, 2006, Myeloma Responses and Tolerance Following Combined Kidney and Nonmyeloablative Marrow Transplantation: In Vivo and In Vitro Analyses, American Journal of Transplantation, 6: 2121-2133.
International Search Report and Written Opinion for International Application No. PCT/US2019/025958, filed Apr. 5, 2019, dated Jul. 2, 2019, 7 pages.
International Search Report and Written Opinion for International Application No. PCT/US2019/051711, filed Sep. 18, 2019, dated Jan. 15, 2020, 9 pages.
Jun. 2007, Adoptive T cell therapy for cancer in clinic, J Clin Invest, 117(6):1466-76, vol. 117.
Kalwak, 2010, Higher CD34+ and CD3+ Cell Doses in the Graft Promote Long-Term Survival, and Have No Impact in the Incidence of Severe Acute or Chronic Graft-versus-Host Disease after In Vivo T Cell-Depleted Unrelated Donor Hematopoietic Stem Cell Transplantation in Children, Biol Blood Marrow Transplant, 16:1388-1401.
Kawai, 2008, HLA-mismatched Renal Transplantation without Maintenance Immunosuppression, New England Journal of Medicine, 358(4):353-361.
Khalil, 2017, Rubbing Against Blood Clots Uding Helical Robots: Modeling and In Vitro Experimental Validation, IEEE Robotics and Automation Letter vol. 2, No. 2, 927-934.
Kohrt, 2009, TLI and ATG Conditioning with Low Risk of Graft-Versus-Host Disease Retains Antitumor Reactions after Allogeneic Hematopoietic Cell Transplantation from Related and Unrelated Donors, Blood, 114(5):1099-1109.
Ledford, 2008, Organ Transplant without Rejection, Nature News, ISSN 0028-0836, EISSN 1476-4687 (3 pages).
Leventhal, 2012, Chimerism and tolerance without GVHD or engraftment syndrome in HLA-mismatched combined kidney and hematopoietic stem cell transplantation, Sci Transl Med. 4(124):1-22.
Leventhal, 2013, Tolerance Induction in HLA Disparate Living Donor Kidney Transplantation by Donor Stem Cell Infusion: durable chimerism predicts outcome, Transplantation, 95(1):169-176.
Mali, 2013, Delivery systems for gene therapy, Indian J Hum Genet. Jan.-Mar. 2013; 19(1): 3-8, 8 pages.
Millan, 2002, Mixed chimerism and immunosuppressive drug withdrawal after HLA-mismatched kidney and hematopoietic progenitor transplantation, Transplantation, 73:1386-1391.

(56) References Cited

OTHER PUBLICATIONS

NG, 2009, Isolation of human and mouse hematopoietic stem cells, Methods Mol Biol., 506:13-21.

Perez-Pujol, 2005, Proteomic analysis of gray platelet syndrome by iTRAQ Labelling and mass spetroscopy: a potential new diagnostic strategy for platelet disorders, Blood, (ASH Annual Meeting Abstracts), 106(11):2161.

Sachs, 2014, Induction of Tolerance through Mixed Chimerism, Cold Spring Harb Perspect Med, 4;4:a015529, 19 pages.

Scandling, 2008, Tolerance and Chimerism after Renal and Hematopoietic-Cell Transplantation, N Engl J Med, 358:362-8.

Scandling, 2012, Tolerance and withdrawal of immunosuppressive drugs in patients given kidney and hematopoietic cell transplants, Am J Transplant., 12(5):1133-45.

Scandling, 2015, Chimerism, Graft Survival, and Withdrawal of Immunosuppressive Drugs in HLA Matched and Mismatched Patients After Living Donor Kidney and Hematopoietic Cell Transplantation, American Journal of Transplantation, 15:695-704.

Slavin, 1977, Induction of specific tissue transplantation tolerance using fractionated total lymphoid irradiation in adult mice: long-term survival of allogeneic bone marrow and skin grafts, J. Exp. Med., 146:34-48.

Spohn, 2015, Automated CD34+ cell isolation of peripheral blood stem cell apheresis product, Cytotherapy, 10:1465-71.

Stanford Team Prevent Kidney Transplant Rejection Without Drugs, ScienceDaily, Apr. 24, 2002, pp. 1-3, downloaded from www.sciencedaily.com/releases/2002/04/020424072642.htm.

Strober, 2011, Translational studies in hematopoietic cell transplantation: treatment of hematologic malignancies as a stepping stone to tolerance induction, Semin Immunol., 23(4):273-81.

Sykes, 2001, Mixed Chimerism and Transplant Tolerance, Immunity, 14:417-424.

Szabolcs, 2012, Tolerance after solid organ and hematopoietic cell transplantation, Biol Blood Marrow Transplant, 18(1):S193-200.

Tatekawa, 2006, A novel direct competitive repopulation assay for human hematopoietic stem cells using NOD/SCID mice, Cytotherapy, vol. 8, No. 4, 390-398.

Urbano-Ispizua, 2001, The number of donor CD3+ cells is the most important factor for graft failure after allogeneic transplantation of CD34+ selected cells from peripheral blood from HLA-identical siblings, Blood,97(2):383-387.

CELLULAR COMPOSITIONS DERIVED FROM PRIOR ORGAN DONORS AND METHODS OF MANUFACTURE AND USE THEREOF

This application is a continuation of U.S. patent application Ser. No. 15/946,124, filed Apr. 5, 2018, the contents of which are incorporated by reference.

FIELD OF THE INVENTION

The invention generally relates to cellular compositions derived from prior organ donors for establishing mixed chimerism and methods of manufacture and use thereof

BACKGROUND

According to the United Network for Organ Sharing, over 150,000 organ transplants from living donors were performed in the United State between 1988 and 2018. Although an organ transplant can save or transform the recipient's life, transplantation remains a risky procedure. A major concern is that the recipient's immune system will identify the transplanted organ as foreign and destroy it. Consequently, most transplant recipients must take immunosuppressive drugs for the rest of their lives. Immunosuppressive therapy, however, carries its own set of risks, including increased risk of infection, cancer, hypertension, and liver damage. In addition, immunosuppression does not guarantee that the recipient will tolerate the graft. For example, even with immunosuppressive therapy, the rate of rejection for kidney transplants, the most common type of solid organ transplant, is about 25%. Consequently, tens of thousands of recipients of live-donor organ transplants receiving immunosuppressive therapy remain at risk of both graft rejection and the side effects of immunosuppression.

SUMMARY

Clinical data from the last decade has shown that long-term graft tolerance in humans without immunosuppression can be achieved by reconstructing the recipient's immune system to comprise a mixture of donor-derived and recipient-derived cells. Mixed chimerism is established by providing donor-derived hematopoietic cellular compositions that include $CD34^+$ and $CD3^+$ cells. The invention recognizes that there is a need for compositions and methods that promote mixed chimerism in patients who have previously received solid organ transplants. In that manner, the invention provides an approach for establishing mixed chimerism in patients that have previously received a solid organ transplant and remain on immunosuppressive therapy. Aspects of the invention are accomplished with cellular products that contain $CD34^+$ cells and $CD3^+$ cells, both of which are derived from an apheresis product obtained from a subject that has previously donated a solid organ. The compositions of the invention are provided to patients that have previously received an organ transplant and remain on immunosuppressive therapy. The compositions of the invention establish mixed chimerism in the patient and allow for the removal of immunosuppressive drugs while still preventing development of graft versus host disease.

Unlike prior methods of establishing mixed chimerism that involved making the cellular compositions as part of an integrated transplantation regimen, the cellular products of the invention are derived from post-surgical apheresis products and can be administered at any point following the transplantation surgery. Mixed chimerism confers several advantages on organ transplant recipients. First, it improves the recipient's chances of tolerating the graft. In addition, it allows transplant recipients to discontinue immunosuppressive therapy, which has several deleterious side effects. To date, induction of mixed chimerism is the only way to maintain long-term graft tolerance in humans without immunosuppression. However, most recipients of solid organ transplants do not establish mixed chimerism because they do not or did not have access to regimens for establishing mixed chimerism at the time of their transplantation procedures. Consequently, in the absence of further treatment, such patients will require immunosuppressive therapy for the remainder of their lives and remain at risk of graft rejection.

The compositions and methods of the invention give solid organ transplant recipients that have not already developed mixed chimerism the opportunity to do so. The cellular products are derived from apheresis products obtained from the donor post-operatively and may be provided to the recipient at any time. Thus, the compositions and methods of the invention are not constrained by the timing or protocol of the organ transplant procedure. As a result, the compositions and methods provided herein allow a vast number of organ transplant recipients to establish mixed chimerism, thereby improving the chances of graft tolerance and allowing the cessation of immunosuppressive therapy.

In an aspect, the invention provides cellular products for establishing mixed chimerism in a recipient of a solid organ transplant from a donor. The cellular products include $CD34^+$ cells and $CD3^+$ cells derived from one or more apheresis products from a subject that has already donated a solid organ. Preferably, the $CD34^+$ cells are present in amount greater than $5 \times 10^5$ $CD34^+$ cells/kg recipient, and the $CD3^+$ cells are present in an amount greater than $1 \times 10^5$ $CD3^+$ cells/kg recipient. Although, the skilled artisan will recognize that other $CD34^+$ and $CD3^+$ cell concentrations are within the scope of the invention, as exemplified throughout the application.

For example, the compositions of the invention can include various concentrations for each of the $CD34^+$ cells and $CD3^+$ cells, and different concentrations are discussed herein. The amount may be specified as a number of cells relative to the body mass of the recipient. For example, the cellular product may contain at least $1 \times 10^5$, $2 \times 10^5$, $5 \times 10^5$, $1 \times 10^6$, $2 \times 10^6$, or $4 \times 10^6$ $CD34^+$ cells/kg recipient weight. The cellular product may contain at least $1 \times 10^4$, $2 \times 10^4$, $5 \times 10^4$, $1 \times 10^5$, $2 \times 10^5$, $5 \times 10^5$, $1 \times 10^6$, $2 \times 10^6$, $5 \times 10^6$, $1 \times 10^7$, $2 \times 10^7$, $5 \times 10^7$, or $1 \times 10^8$ $CD3^+$ cells/kg recipient weight.

The apheresis product may be obtained at any point after the subject has donated a solid organ. For example, the apheresis product may be obtained at least 1 day, at least 2 days, at least 3 days, at least 4 days, at least 5 days, at least 1 week, at least 2 weeks, at least 4 weeks, at least 8 weeks, at least 12 weeks, at least 24 weeks, at least 1 year, at least 2 years, or at least 5 years after the subject has donated a solid organ.

The apheresis product may be obtained from a subject who donated the solid organ to the recipient. The apheresis product may be obtained from a subject who is different from the donor who donated the solid organ to the recipient.

The solid organ may be any solid organ that can be transplanted according to methods known in the art. For example and without limitation, the solid organ may be a kidney, lung, pancreas, pancreatic, islet cells, heart, intestine, colon, liver, skin, muscle, gum, eye, or tooth. Preferably, the solid organ is a kidney.

The CD34$^+$ cells, the CD3$^+$ cells, or both may be HLA-matched to the recipient. The CD34$^+$ cells, the CD3$^+$ cells, or both may be HLA-mismatched to the recipient. The donor and recipient may be HLA-matched at six, eight, ten, or twelve alleles among the HLA-A, HLA-B, HLA-C, HLA-DP, HLA-DQ, and HLA-DR genes. The donor and recipient may be HLA-mismatched at one, two, three, four, five, six, or more alleles among the HLA-A, HLA-B, HLA-C, HLA-DP, HLA-DQ, and HLA-DR genes.

The CD34$^+$ cells and CD3$^+$ cells may be obtained from a single apheresis product. The CD34$^+$ cells and CD3$^+$ cells may be obtained from multiple apheresis products, for example, two, three, four, five, six, or more apheresis products. The CD34$^+$ cells and CD3$^+$ cells may be obtained from a cryopreserved apheresis product. The CD34$^+$ cells may be purified prior to cryopreservation or after cryopreservation.

The cellular product may be cryopreserved. The cellular product may contain one or more cryoprotectants. The cryoprotectant may be dextran having an average molecular weight of 40,000 Da or DMSO. The cellular product may contain the cryoprotectant at a concentration of about 1%, 2%, 3%, 4%, 5%, 7.5%, or 10%.

The CD34$^+$ cells and CD3$^+$ cells may be provided in separate containers. The CD34$^+$ cells and CD3$^+$ cells may be provided as a mixture in the same container.

In an aspect, the invention provided methods for manufacturing a cellular product for establishing mixed chimerism in a recipient of a solid organ transplant from a donor. The methods include receiving at least one apheresis product containing CD34$^+$ cells and CD3$^+$ cells from a subject after the subject has donated the solid organ; purifying a first portion of the at least one apheresis product to obtain an enriched amount of CD34$^+$ cells; and retaining a second portion of the sample comprising CD3$^+$ cells.

The method may include mixing the enriched amount of CD34$^+$ cells with the second portion of the sample comprising CD3$^+$ cells. The method may include maintaining the enriched amount of CD34$^+$ cells and the second portion of the sample comprising CD3$^+$ cells in separate containers.

The method may include any feature described above in relation to the compositions of the invention.

In an aspect, the invention provides methods for establishing mixed chimerism in a recipient of a solid organ transplant from a donor. The methods include administering a cellular product for establishing mixed chimerism to the recipient of a solid organ transplant after the recipient has already undergone a solid organ transplant procedure, the cellular product being derived from an apheresis product obtained from a subject that has undergone a solid organ transplant procedure.

The method may include any feature described above in relation to the compositions of the invention.

DETAILED DESCRIPTION

The primary hurdle in organ transplantation is getting the recipient to tolerate the donor's tissue. If the recipient's immune system detects the donated organ as foreign, it attacks the tissue, leading to graft rejection. Consequently, most transplant recipients must take drugs that suppress the immune system. Immunosuppressive therapy, however, creates its own set of risks. For example, immunosuppressive drugs decrease the body's ability to ward off infections. In addition, because they hinder the immune system's ability to identify and destroy malignant tissue, immunosuppressive drugs increase the risk of developing cancer.

To avoid graft rejection, transplantation of solid organs may be accompanied by transfer of donor-derived blood cell progenitors. Providing donor blood cells allows reconstitution of the recipient's immune system to include cells that have been educated to recognize the organ as non-foreign tissue. Consequently, the donated organ is not attacked, and the recipient tolerates the graft.

One strategy for reconstructing the recipient's immune system entails complete replacement of the recipient's hematopoietic system with exclusively donor-derived cells to achieve a state of full chimerism. A risk associated with full chimerism, however, is that the completely donor-derived immune system may identify the recipient's tissue as foreign and attack it, a condition called graft-versus-host disease (GVHD). See, e.g., Sach et al., Induction of Tolerance through Mixed Chimerism, Cold Spring Harb Perspect Med 2014; 4:a015529, doi: 10.1101/cshperspect.a015529, the contents of which are incorporated herein by reference. As a result, fully chimeric patients must remain on immunosuppressive therapy indefinitely.

Another strategy is to repopulate the recipient's immune system with a mixture of donor-derived cells and recipient-derived cells to attain a state called mixed chimerism. Compared to full chimerism, mixed chimerism is associated with lower rates of GVHD. In addition, mixed chimeric regimens require lower doses of immunosuppressive therapy initially and allow complete discontinuation of immunosuppression after the stability of the recipient's mixed chimerism has been established. To date, induction of mixed chimerism is the only method of producing graft tolerance in humans without maintaining immunosuppressive therapy.

There are many transplant recipients who have not established mixed chimerism. For example, many patients undergo transplantation regimens that are not intended to induce mixed chimerism. For others, mixed chimerism was a goal of transplantation that was not achieved. In either case, a supply of donor-derived hematopoietic cells may no longer be available. For example, donor blood cells may not have been collected from the donor prior to transplantation surgery, or a supply of donor blood cells that was collected has already been consumed.

The compositions and methods of the invention provide patients that have already undergone solid organ transplantation an opportunity to establish mixed chimerism. The compositions include CD34$^+$ cells and CD3$^+$ cells derived from an apheresis product taken from a subject that has already donated a solid organ.

Cellular Products

All blood cells, including the cells of the immune system, are derived from hematopoietic stem cells (HSCs). HSCs are multipotent cells that can differentiate into various specialized cells and also reproduce to generate new HSCs. HSCs that differentiate form either lymphoid progenitors or myeloid progenitors. Lymphoid progenitors give rise to lymphocytes and natural killer cells. Myeloid progenitors produce cells of the myeloid and erythroid lineages, such as erythrocytes, platelets, basophils, neutrophils, eosinophils, monocytes, macrophages, and antigen-presenting cells, such as dendritic cells. In adults, most hematopoietic development occurs in the bone marrow, although maturation and activation of some lymphoid cells occurs in the spleen, thymus, and lymph nodes.

The cellular products of the invention include two populations of cells that allow donor HSCs to develop into mature cells of the immune system in the recipient's body. One population includes CD34$^+$ cells. CD34 is a cell surface marker that is expressed in HSCs and their immediate descendants, multipotent progenitor cells, which have not committed to either the myeloid or lymphoid lineage. Consequently, CD34 expression is a useful measure for identifying populations of cells that contain HSCs. The other population includes CD3$^+$ cells. CD3 comprises a group of polypeptides that interact with the two polypeptide chains of the T cell receptor to form the T cell receptor complex. The CD3 complex includes a gamma chain, delta chain, and two epsilon chains. CD3 is expressed on the surface of mature T cells and is thus useful as a marker for T cells.

To promote establishment of mixed chimerism in the recipient, the cellular products include CD34$^+$ cells and CD3$^+$ cells in appropriate quantities. For example, an ample supply of CD34$^+$ cells is necessary to develop a stable population of donor-derived immune cells in the recipient. However, CD34$^+$ cells are relatively scarce, making up only about 0.1-0.2% of peripheral blood cells in normal, untreated patients. Therefore, the cellular products may contain CD34$^+$ cells that have been purified from an apheresis product to obtain a sufficient number of such cells. For example, the CD34$^+$ cells may be purified using an immunomagnetic column system, as described below. In contrast, CD3$^+$ cells are abundant, accounting for a majority of mononuclear cells in the peripheral blood. Thus, the population of CD3$^+$ cells in the cellular products may be obtained from a portion of the apheresis product that has not been subjected to a column purification step. Alternatively or additionally, CD3$^+$ cells may be obtained from a residual fraction following purification of CD34$^+$ cells, such as the effluent of a column used to purify CD34$^+$ cells.

The cellular products may contain CD34$^+$ cells and CD3$^+$ cells in defined amounts. A useful unit of cell quantity in a product is the number of cells relative to the body mass of the recipient. For example and without limitation, the cellular product may contain at least $1\times10^4$, $2\times10^4$, $5\times10^4$, $1\times10^5$, $2\times10^5$, $5\times10^5$, $1\times10^6$, $2\times10^6$, or $4\times10^6$, $1\times10^7$, $2\times10^7$, $4\times10^7$, or $1\times10^8$ CD34$^+$ cells/kg recipient weight. For example and without limitation, the cellular product may contain at least $1\times10^4$, $2\times10^4$, $5\times10^4$, $1\times10^5$, $2\times10^5$, $5\times10^5$, $1\times10^6$, $2\times10^6$, $5\times10^6$, $1\times10^7$, $2\times10^7$, $5\times10^7$, or $1\times10^8$ CD3$^+$ cells/kg recipient weight. Other concentrations are exemplified in each of Strober et al., U.S. Pat. No. 9,504,717 and Strober et al., U.S. Pat. No. 9,561,253, the content of each of which is incorporated by reference herein in its entirety.

The cellular product may contain CD34$^+$ cells at a designated level of purity. For example, the cellular product may contain CD34$^+$ cells that are at least 30%, at least 40%, at least 50%, at least 60%, at least 70%, at least 80%, at least 90%, at least 95%, at least 98%, or at least 99% pure. Other purities are exemplified in each of Strober et al., U.S. Pat. No. 9,504,717 and Strober et al., U.S. Pat. No. 9,561,253, the content of each of which is incorporated by reference herein in its entirety.

The CD34$^+$ cells and CD3$^+$ cells may be derived from any subject that has donated a solid organ. The CD34$^+$ cells and CD3$^+$ cells may be from the same subject. The CD34$^+$ cells and CD3$^+$ cells may be from different subjects. Preferably, the CD34$^+$ cells and CD3$^+$ cells are derived from the subject that donated the solid organ that has been transplanted into the recipient.

The CD34$^+$ cells and CD3$^+$ cells may be provided as a mixture in one or more containers. The CD34$^+$ cells and CD3$^+$ cells may be provided in separate container. Any commercially available container approved to hold cellar products may be used.

The cellular product may be provided frozen. Consequently, the cellular product may contain a cryoprotectant. Any cryoprotectant known in the art may be used. For example and without limitation, the cryoprotectant may be DMSO, dextran having an average molecular weight of 40 kDa, serum, e.g., bovine serum, albumin, e.g., human serum albumin, or cell culture medium. The cryoprotectant may be present at a defined concentration. For example, the cellular product may contain about 1% DMSO, about 2% DMSO, about 5% DMSO, about 7.5% DMSO, about 10% DMSO, about 12.5% DMSO, about 15% DMSO, or about 20% DMSO. The cellular product may contain about 1% dextran, about 2% dextran, about 5% dextran, about 7.5% dextran, about 10% dextran, about 12.5% dextran, about 15% dextran, or about 20% dextran. Cyroprotection is discussed in each of Strober et al., U.S. Pat. No. 9,504,717 and Strober et al., U.S. Pat. No. 9,561,253, the content of each of which is incorporated by reference herein in its entirety.

The cellular product may contain agents that enhance engraftment or functional mobilization of the hematopoietic cells in the recipient. The cellular product may contain agents that prevent a negative reaction of the recipient to the hematopoietic cells. For example and without limitation, the pharmaceutical composition may contain a cytokine, chemokine, growth factor, excipient, carrier, antibody or a fragment thereof, small molecule, drug, agonist, antagonist, matrix protein, or complementary cell type.

The cellular product may contain a buffer. The cellular product may be buffer to maintain physiologically compatible pH. For example, the cellular product may be buffered to a neutral pH, such as from about 6.0 to about 8.0.

The cellular product can be supplied in the form of a pharmaceutical composition, comprising an isotonic excipient prepared under sufficiently sterile conditions for human administration. Choice of the cellular excipient and any accompanying elements of the composition is adapted in accordance with the route and device used for administration. For general principles in medicinal formulation, see Cell Therapy: Stem Cell Transplantation, Gene Therapy, and Cellular Immunotherapy, by G. Morstyn & W. Sheridan. eds., Cambridge University Press, 1996; and Hematopoietic Stem Cell Therapy, E. D. Ball, J. Lister & P. Law, Churchill Livingstone, 2000.

The CD34$^+$ cells, CD3$^+$ cells, or both may be HLA-matched or HLA-mismatched to the recipient. Human leukocyte antigens (HLAs), also called major histocompatibility complex (MHC) antigens, are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells.

A key aspect of the HLA gene system is its polymorphism. Each gene exists in different alleles. Allelic gene products differ in one or more amino acids in the alpha and/or beta domain(s). An individual has two alleles of each gene, for a total of twelve alleles among the HLA-A, HLA-B, HLA-C, HLA-DP, HLA-DQ, and HLA-DR genes. An HLA-matched donor may have a match with the recipient at six, eight, ten, or twelve alleles selected from any combination of the HLA-A, HLA-B, HLA-C, HLA-DP, HLA-DQ, and HLA-DR genes. The genes most important for HLA typing are HLA-A, HLA-B, and HLA-DR, so the donor and recipient may be matched at all six alleles of the HLA-A, HLA-B, and HLA-DR genes. An HLA-mismatched donor may have a mismatch at one, two, three, four, five, six, or more alleles among the HLA-A, HLA-B, HLA-C, HLA-DP, HLA-DQ, and HLA-DR genes. HLA typing may be performed by any method known in the art. Examples of HLA typing methods include serological cytotoxicity, flow cytometry, and DNA typing. Such methods are described in, for example, U.S. Pat. No. 9,561,253, the contents of which are incorporated herein by reference.

The HLA genes are clustered in a super-locus present on chromosome position 6p21. Consequently, the set of alleles present on a single chromosome, i.e., a haplotype, tends to be inherited as a group. Identifying a patient's haplotypes can help predict the probability of finding matching donors and assist in developing a search strategy. Haplotypes vary in how common they are among the general population and in their frequency within different racial and ethnic groups.

Numerous exemplary embodiments are now described below, both HLA matched and HLA mismatched. The skilled artisan will recognize that the below embodiments are exemplary and non-limiting, particularly, the below embodiments do not limit any other part or exemplified cell amounts or combinations in any other part of this application.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $1\times10^5$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $2\times10^5$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $5\times10^5$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $1\times10^6$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $2\times10^6$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $5\times10^6$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $1\times10^7$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $2\times10^7$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $5\times10^7$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $5\times10^5$ $CD34^+$ cells/kg recipient weight and $CD3^+$ cells derived from an apheresis product obtained from a subject that has previous donated a solid organ in an amount of at least $1\times10^8$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $1\times10^6$ $CD34^+$ cells/kg recipient weight and $CD3^+$ cells derived from an apheresis product obtained from a subject that has previous donated a solid organ in an amount of at least $1\times10^5$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $1\times10^6$ $CD34^+$ cells/kg recipient weight and $CD3^+$ cells derived from an apheresis product obtained from a subject that has previous donated a solid organ in an amount of at least $2\times10^5$ $CD3^+$ cells/kg recipient weight, the $CD34^+$ cells and $CD3^+$ cells being HLA-matched to the recipient.

The cellular product may contain $CD34^+$ cells derived from an apheresis product obtained from a subject that has previous donated a solid organ in an amount of at least $1\times10^6$ $CD34^+$ cells/kg recipient weight and $CD3^+$ cells derived from an apheresis product obtained from a subject that has previous donated a solid organ in an amount of at least $5\times10^5$ $CD3^+$ cells/kg recipient weight, the $CD34^+$ cells and $CD3^+$ cells being HLA-matched to the recipient.

The cellular product may contain CD34$^+$ cells derived from an apheresis product obtained from a subject that has previous donated a solid organ in an amount of at least $1\times10^6$ CD34$^+$ cells/kg recipient weight and CD3$^+$ cells derived from an apheresis product obtained from a subject that has previous donated a solid organ in an amount of at least $1\times10^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $1\times10^6$ CD34$^+$ cells/kg recipient weight and CD3$^+$ cells derived from an apheresis product obtained from a subject that has previous donated a solid organ in an amount of at least $2\times10^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $1\times10^6$ CD34$^+$ cells/kg recipient weight and CD3$^+$ cells derived from an apheresis product obtained from a subject that has previous donated a solid organ in an amount of at least $5\times10^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $1\times10^6$ CD34$^+$ cells/kg recipient weight and CD3$^+$ cells derived from an apheresis product obtained from a subject that has previous donated a solid organ in an amount of at least $1\times10^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $1\times10^6$ CD34$^+$ cells/kg recipient weight and CD3$^+$ cells derived from an apheresis product obtained from a subject that has previous donated a solid organ in an amount of at least $2\times10^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $1\times10^6$ CD34$^+$ cells/kg recipient weight and CD3$^+$ cells derived from an apheresis product obtained from a subject that has previous donated a solid organ in an amount of at least $5\times10^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $1\times10^6$ CD34$^+$ cells/kg recipient weight and CD3$^+$ cells derived from an apheresis product obtained from a subject that has previous donated a solid organ in an amount of at least $1\times10^8$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $1\times10^5$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $2\times10^5$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $5\times10^5$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $1\times10^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $2\times10^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $5\times10^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $1\times10^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $2\times10^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $5\times10^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $1\times10^8$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 1×10$^5$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 2×10$^5$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 5×10$^5$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 1×10$^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 2×10$^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 5×10$^6$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 1×10$^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 2×10$^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 5×10$^7$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 4×10$^6$ CD34$^+$ cells/kg recipient weight and CD3$^+$ cells derived from an apheresis product obtained from a subject that has previous donated a solid organ in an amount of at least 1×10$^8$ CD3$^+$ cells/kg recipient weight, the CD34$^+$ cells and CD3$^+$ cells being HLA-matched to the recipient.

The cellular product may contain CD34$^+$ cells derived from an apheresis product obtained from a subject that has previous donated a solid organ in an amount of at least 5×10$^5$ CD34$^+$ cells/kg recipient weight and CD3$^+$ cells derived from an apheresis product obtained from a subject that has previous donated a solid organ in an amount of at least 1×10$^5$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least 5×10$^5$ CD34$^+$ cells/kg recipient weight and CD3$^+$ cells derived from an apheresis product obtained from a subject that has previous donated a solid organ in an amount of at least 2×10$^5$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least 5×10$^5$ CD34$^+$ cells/kg recipient weight and CD3$^+$ cells derived from an apheresis product obtained from a subject that has previous donated a solid organ in an amount of at least 5×10$^5$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least 5×10$^5$ CD34$^+$ cells/kg recipient weight and CD3$^+$ cells derived from an apheresis product obtained from a subject that has previous donated a solid organ in an amount of at least 1×10$^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least 5×10$^5$ CD34$^+$ cells/kg recipient weight and CD3$^+$ cells derived from an apheresis product obtained from a subject that has previous donated a solid organ in an amount of at least 2×10$^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least 5×10$^5$ CD34$^+$ cells/kg recipient weight and CD3$^+$ cells derived from an apheresis product obtained from a subject that has previous donated a solid organ in an amount of at least 5×10$^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least 5×10$^5$ CD34+ cells/kg recipient weight and CD3+ cells derived from an apheresis product obtained from a subject that has previous donated a solid organ in an amount of at least $1\times10^7$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $5\times10^5$ CD34+ cells/kg recipient weight and CD3+ cells derived from an apheresis product obtained from a subject that has previous donated a solid organ in an amount of at least $2\times10^7$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $5\times10^5$ CD34+ cells/kg recipient weight and CD3+ cells derived from an apheresis product obtained from a subject that has previous donated a solid organ in an amount of at least $5\times10^7$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $5\times10^5$ CD34+ cells/kg recipient weight and CD3+ cells derived from an apheresis product obtained from a subject that has previous donated a solid organ in an amount of at least $1\times10^8$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $1\times10^5$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $2\times10^5$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $5\times10^5$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $1\times10^6$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $2\times10^6$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $5\times10^6$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $1\times10^7$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $2\times10^7$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $5\times10^7$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $1\times10^6$ CD34+ cells/kg recipient weight and CD3+ cells derived from an apheresis product obtained from a subject that has previous donated a solid organ in an amount of at least $1\times10^8$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $2\times10^6$ CD34+ cells/kg recipient weight and CD3+ cells derived from an apheresis product obtained from a subject that has previous donated a solid organ in an amount of at least $1\times10^5$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $2\times10^6$ CD34+ cells/kg recipient weight and CD3+ cells derived from an apheresis product obtained from a subject that has previous donated a solid organ in an amount of at least $2\times10^5$ CD3+ cells/kg recipient weight, the CD34+ cells and CD3+ cells being HLA-mismatched to the recipient.

The cellular product may contain CD34+ cells derived from an apheresis product obtained from a subject that has previous donated a solid organ in an amount of at least $2\times10^6$ CD34+ cells/kg recipient weight and CD3+ cells derived from an apheresis product obtained from a subject that has previous donated a solid organ in an amount of at least $5\times10^5$ CD3+ cells/kg recipient weight, the CD34+ cells and CD3+ cells being HLA-mismatched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $1\times10^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $2\times10^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $5\times10^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $1\times10^7$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $2\times10^7$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $5\times10^7$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $2\times10^6$ CD34$^+$ cells/kg recipient weight and CD3$^+$ cells derived from an apheresis product obtained from a subject that has previous donated a solid organ in an amount of at least $1\times10^8$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $1\times10^5$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $2\times10^5$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $5\times10^5$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $1\times10^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $2\times10^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $5\times10^6$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $1\times10^7$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $2\times10^7$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $5\times10^7$ CD3$^+$ cells/kg recipient weight, the CD34$^+$ cells and CD3$^+$ cells being HLA-mismatched to the recipient.

The cellular product may contain CD34$^+$ cells derived from an apheresis product obtained from a subject that has previous donated a solid organ in an amount of at least $4\times10^6$ CD34$^+$ cells/kg recipient weight and CD3$^+$ cells derived from an apheresis product obtained from a subject that has previous donated a solid organ in an amount of at least $1\times10^8$ $CD3^+$ cells/kg recipient weight, the $CD34^+$ cells and $CD3^+$ cells being HLA-mismatched to the recipient.

Preparation of Cellular Products

The cellular products of the invention are prepared from one or more apheresis products. In certain embodiments, the one or more apheresis products may be divided into two portions: one portion for purification of $CD34^+$ cells, and one portion to serve as the source of $CD3^+$ cells. Alternatively, the one or more apheresis products may be used as a single portion. When multiple apheresis products are used, they may be combined and then divided into portions. Alternatively, individual apheresis products can be divided into portions, and the portions from individual apheresis products can be combined. Other manufacturing methods, using column effluent for obtaining $CD3^+$ cells are described for example in Strober et al., U.S. Pat. Nos. 9,504,717 and 9,561,253, the content of each of which is incorporated by reference herein in its entirety.

Preferably, the apheresis products are obtained from the donor of the solid organ that has been transplanted into the recipient. Apheresis methods are known in the art and described in, for example, U.S. Pat. No. 9,561,253, the contents of which are incorporated herein by reference.

As indicated above, $CD34^+$ cells make up a low percentage of peripheral blood cells in normal subjects. However, the fraction of $CD34^+$ cells in blood can be increased by administering to the subject a factor, such as granulocyte colony stimulating factor (G-CSF), that mobilizes $CD34^+$ cells from bone marrow and other sources. Thus, prior to apheresis, the subject may be given G-CSF to mobilize $CD34^+$ cells. Regimens for administering G-CSF to a subject prior to apheresis, including the dosage, frequency, and timing of administration, are known in the art and described in, for example, U.S. Pat. No. 9,561,253, the contents of which are incorporated herein by reference.

During preparation of the cellular products of the invention, cells may be frozen at any stage. For example, cells may be frozen immediately after an apheresis product is isolated from a donor but prior to separation into portions, after separation into portions, after purification or enrichment of $CD34^+$ cells, or after combining purified $CD34^+$ cells with $CD3^+$ cells.

Cryopreservation of compositions of the invention may include addition of a cryoprotectant, such as a cryoprotectant described above. Cryopreservation typically involves reducing the temperature of the cell-containing sample at a controlled rate. Cryopreservation may include thawing the cell-containing sample and washing the sample to remove one or more cryoprotectants. Methods and reagents for cryopreservation, including freezing, thawing, and washing samples, are known in the art and described in, for example, U.S. Pat. No. 9,561,253, the contents of which are incorporated herein by reference.

$CD34^+$ cells may be purified based on qualitative or quantitative expression of one or more cell surface markers. Examples of suitable cell surface markers include CD34, Thy-1, CD38, and AC133. $CD34^+$ cells may be purified based on the presence or absence of a marker or on the level of expression of a marker, e.g., high vs. low.

$CD34^+$ cells may be purified by selectively binding a suitable affinity reagent to CD34 or another marker. The affinity reagent may be an antibody, a full-length antibody, a fragment of an antibody, a naturally occurring antibody, a synthetic antibody, an engineered antibody, a full-length affibody, a fragment of an affibody, a full-length affilin, a fragment of an affilin, a full-length anticalin, a fragment of an anticalin, a full-length avimer, a fragment of an avimer, a full-length DARPin, a fragment of a DARPin, a full-length fynomer, a fragment of a fynomer, a full-length kunitz domain peptide, a fragment of a kunitz domain peptide, a full-length monobody, a fragment of a monobody, a peptide, a polyaminoacid, or the like. The affinity reagent may be directly conjugated to a detection reagent and/or purification reagent. The detection reagent and purification reagent may be the same, or they may be different. For example, the detection reagent and/or purification reagent may be fluorescent, magnetic, or the like. The detection reagent and/or purification reagent may be a magnetic particle for column purification, e.g., an immunomagnetic microsphere.

$CD34^+$ cells may be isolated, enriched, or purified by any method. For example, $CD34^+$ cells may be isolated, enriched, or purified by column purification, flow cytometery, cell sorting, or immunoadsorption column separation. Preferably, $CD34^+$ cells are purified using an immunomagnetic column system, such as those sold under the trade name CliniMACS by Miltenyi Biotec Inc. (Auburn, Calif.), Methods of affinity purification of hematopoietic cells, including $CD34^+$ cells, and analysis of purified populations are described in, for example, U.S. Pat. Nos. 9,561,253; 9,452,184; Ng et al., Isolation of human and mouse hematopoietic stem cells, Methods Mol Biol. (2009) 506:13-21. doi: 10.1007/978-1-59745-409-4_2; and Spohn et al., Automated $CD34^+$ cell isolation of peripheral blood stem cell apheresis product, Cytotherapy (2015) October; 17(10): 1465-71. doi: 10.1016/j.jcyt.2015.04.005, the contents of each of which are incorporated herein by reference. The methods may include positive selection, negative selection, or both.

$CD3^+$ cells may be obtained by dividing one or more apheresis products into two portions, using one portion to purify or enrich $CD34^+$ cells, and using the second portion as a source of $CD3^+$ cells. Alternatively, $CD3^+$ cells may be obtained from a portion from which $CD34^+$ cells have been purified, such as the effluent of column used to purify $CD34^+$ cells, as described in, for example, U.S. Pat. No. 9,561,253, the contents of which are incorporated herein by reference.

$CD34^+$ cells and/or $CD3^+$ cells may be expanded ex vivo. Expansion may occur prior to, or subsequent to, freezing. Expansion may include providing one or more growth factors, and it may include culturing cells in the presence of another cell type, e.g., feeder cells. Methods for expanding hematopoietic cells are described in, for example, U.S. Pat. No. 9,561,253, the contents of which are incorporated herein by reference.

Providing Cellular Products

The cellular products of the invention may be provided to the recipient of a solid organ transplant. The cellular product may be provided by any suitable means. For example and without limitation, the $CD34^+$ cells and/or $CD3^+$ cells may be delivered to the recipient by injection using a needle, catheter, central line or the like. In some cases, the cells may be delivered intravascularly, intravenously, intraarterially, subcutaneously, intramuscularly, directly to the bone, or through any source which permits the hematopoietic cells to home to an appropriate site in the recipient such that the hematopoietic cells persist, regenerate and differentiate in the recipient. The $CD34^+$ cells and/or $CD3^+$ cells may be provided by infusion. The $CD34^+$ cells and/or $CD3^+$ cells may be provided in an inpatient procedure or in an outpatient procedure. An inpatient procedure requires admission to a hospital, and the patient may spend one or more nights in the hospital. An outpatient procedure does not require admission to a hospital and may be performed in a non-hospital setting, such as a clinic, doctor's office, home, or other location.

The compositions of the invention may be used in conjunction with transplantation of any solid organ. For example and without limitation, the solid organ may be a kidney, lung, pancreas, pancreatic, islet cells, heart, intestine, colon, liver, skin, muscle, gum, eye, or tooth. The transplant may include a complete organ, a portion of an organ, or cells from a tissue of an organ. The cellular product may be provided prior to, during, or subsequent to the solid organ transplant. For example and without limitation, the cellular product may be provided one, two, three, four, five, or six days or one, two, three, or four weeks prior to the solid organ transplant, or it may be provided one, two, three, four, five, or six days or one, two, three, or four weeks after the solid organ transplant.

To facilitate establishment of mixed chimerism in the recipient, the recipient's immune system may be conditioned in conjunction with providing the cellular product. For example, non-myeloablative conditioning may be used. In non-myeloablative conditioning, the recipient is exposed to drugs, antibodies, irradiation, or some combination thereof at a dose that is too low to eradicate all the bone marrow cells. Typically, the conditioning regimen includes treatment with anti-thymocyte globulin (ATG), total lymphoid irradiation, and corticosteroids (e.g. prednisone) for a period of from about 10 to 12 days (e.g. for about 11 days). The irradiation may be targeted to a particular location of the recipient's body. For example, irradiation may be targeted to a tissue, an organ, a region of the body or the whole body. Irradiation may be targeted to the lymph nodes, the spleen, or the thymus or any other area known to a person of skill in the art. When multiple doses of irradiation are administered, the doses may be targeted to the same location or to different locations. Non-myeloablative conditioning may include the use of a T cell depleting agent, such as a monoclonal antibody or drug, e.g., fludarabine. Regimens for non-myeloablative conditioning are known in the art and are described in, for example, U.S. Pat. No. 9,561,253, the contents of which are incorporated herein by reference.

The methods may include immunosuppressive therapy. Immunosuppressive therapy, or immunosuppression, involves treatment of the graft recipient with agents that diminish the response of the host immune system against the donor cells, which can lead to graft rejection. Primary immunosuppressive agents include calcineurin inhibitors, such as tacrolimus, cyclosporin A. Adjuvant agents are usually combined with a calcineurin inhibitor. Adjuvant agents include steroids, azathioprine, mycophenolic acid (MPA) agents, such as mycophenolate mofetil, mTOR inhibitors, such as sirolimus, and belatacept. The use of adjuvant agents allows clinicians to achieve adequate immunosuppression while decreasing the dose and toxicity of individual agents. Antibody-based therapy may use monoclonal (e.g., muromonab-CD3) or polyclonal antibodies or anti-CD25 antibodies (e.g., basiliximab, daclizumab). Antibody-based therapy allows for avoidance or dose reduction of calcineurin inhibitors, possibly reducing the risk of nephrotoxicity. Regimens for immunosuppressive therapy are known in the art and are described in, for example, U.S. Pat. No. 9,561,253, the contents of which are incorporated herein by reference.

Immunosuppression may also diminish the response of the donor immune cells against recipient tissue, which can lead to GVHD. GVHD may be acute or chronic. Acute GVHD typically occurs in the first 3 months after graft and may involve the skin, intestine, or the liver. Treatment for acute GVHD usually includes high-dose corticosteroids such as prednisone. Chronic GVHD typically occurs after the first 3 months following transplant and is the major source of late treatment-related complications. Chronic GVHD may cause functional disability and require prolonged immunosuppressive therapy.

Immunosuppressive therapy may occur in multiple phases. For example, the immunosuppressive regimen may have an induction phase and a maintenance phase. Induction and maintenance phase strategies may use different medicines at doses adjusted to achieve target therapeutic levels to enhance establishment of mixed chimerism in the recipient.

Immunosuppressive therapy may be withdrawn after stable mixed chimerism has been established in the recipient. The chimeric status of the recipient may be monitored as described below and deemed stable after a certain period, for example, 3 months, 6 months 12 months, 18 months, 24 months, or longer. Thus, immunosuppression may be discontinued for the recipients after a certain period, for example, 3 months, 6 months 12 months, 18 months, 24 months, or longer. Withdrawal of immunosuppressive therapy may include tapering, i.e., progressively reducing the dosage or frequency of treatment.

A determination of whether an individual is a full chimera, mixed chimera, or non-chimera made be made by an analysis of a hematopoietic cell sample from the solid organ transplant recipient, e.g. peripheral blood, bone marrow, etc. as known in the art. Analysis may be done by any convenient method of typing. Analysis may be performed on hematopoietic cells or a subset thereof, such as all mononuclear cells, T cells, B cells, $CD56^+$NK cells, and $CD15^+$ neutrophils. Chimerism can be assessed by PCR analysis of microsatellites. For example, commercial kits that distinguish polymorphisms in short terminal repeat lengths of donor and host origin are available. Automated readers provide the percentage of donor type cells based on standard curves from artificial donor and host cell mixtures.

Recipients may be categorized as fully chimeric, mixed chimeric, or non-chimeric based on the fraction of cells that are derived from the donor. For example, recipients can be deemed fully chimeric if they have at least 90%, at least 95%, at least 98%, or at least 99% donor-derived cells. Recipients can be deemed mixed chimeric if they have too few donor-derived cells to be categorized as fully chimeric but a fraction of donor-derived cells that exceeds a certain threshold, such as at least 0.5%, at least 1%, at least 2%, at least 3%, at least 5%, at least 7.5%, at least 10% donor-derived cells. Recipients can be deem non-chimeric if the fraction of donor-derived cells falls below the threshold required to be categorized as mixed chimeric.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information,

What is claimed is:

1. A method for establishing mixed chimerism in a recipient of a solid organ transplant from a subject, the method comprising administering at least one cellular product for establishing mixed chimerism to a recipient of a solid organ transplant after the recipient has already undergone a solid organ transplant procedure, wherein the cellular product is derived from at least one apheresis product obtained from a subject that has donated the transplanted solid organ, and wherein the apheresis product is obtained from the subject at least one day after the subject has donated the solid organ.

2. The method of claim 1, wherein the apheresis product is obtained from the subject at least four days after the subject has donated the solid organ.

3. The method of claim 1, wherein the apheresis product is obtained from the subject at least one year after the subject has donated the solid organ.

4. The method of claim 1, wherein the at least one cellular product comprises $CD34^+$ cells derived from the at least one apheresis product and $CD3^+$ cells derived from the at least one apheresis product.

5. The method of claim 4, wherein the at least one cellular product comprises:
   greater than $5 \times 10^5$ $CD34^+$ cells/kg recipient weight; and
   greater than $1 \times 10^5$ $CD3^+$ cells/kg recipient weight.

6. The method of claim 5, wherein the $CD34^+$ cells and the $CD3^+$ cells are HLA-matched to the solid organ transplant recipient.

7. The method of claim 6, wherein the $CD34^+$ cells and the $CD3^+$ cells are HLA-matched at alleles of HLA-A, HLA-B, and HLA-DR genes.

8. The method of claim 5, wherein the $CD34^+$ cells and the $CD3^+$ cells are HLA-mismatched to the solid organ transplant recipient.

9. The method of claim 8, wherein the $CD34^+$ cells and the $CD3^+$ cells are HLA-mismatched at least one allele of a gene selected from the group consisting of HLA-A, HLA-B, and HLA-DR.

10. The method of claim 4, wherein the $CD34^+$ cells and the $CD3^+$ cells are derived from a single apheresis product.

11. The method of claim 4, wherein the $CD34^+$ cells and the $CD3^+$ cells are derived from multiple apheresis products.

12. The method of claim 4, wherein the at least one cellular product comprises at least one cryoprotectant.

13. The method of claim 12, wherein the at least one cryoprotectant is selected from the group consisting of dimethyl sulfoxide (DMSO) and dextran having an average molecular weight of 40,000 Da.

14. The method of claim 1, comprising administering a plurality of cellular products to the recipient.

15. The method of claim 1, wherein the solid organ is a kidney.

16. The method of claim 1, further comprising:
   receiving the at least one apheresis product; and
   manufacturing the at least one cellular product from the at least one apheresis product.

17. The method of claim 16, wherein the manufacturing step comprises:
   purifying a first portion of the at least one apheresis product to obtain an enriched amount of $CD34^+$ cells; and
   retaining a second portion of the sample comprising $CD3^+$ cells.

18. The method of claim 17, wherein the manufacturing step comprises:
   mixing the enriched amount of $CD34^+$ cells with the second portion of the sample comprising $CD3^+$ cells.

19. The method of claim 18, wherein the manufacturing step comprises:
   maintaining the enriched amount of $CD34^+$ cells and the second portion of the sample comprising $CD3^+$ cells in separate containers.

\* \* \* \* \*